United States Patent

Hanson

Patent Number: 5,267,955
Date of Patent: Dec. 7, 1993

[54] ATHERECTOMY DEVICE

[75] Inventor: Donald W. Hanson, Chanhassen, Minn.

[73] Assignee: Lake Region Manufacturing Company, Inc., Chaska, Minn.

[21] Appl. No.: 914,793

[22] Filed: Jul. 16, 1992

Related U.S. Application Data

[63] Continuation of Ser. No. 521,413, May 10, 1990, abandoned.

[51] Int. Cl.[5] .............................................. A61B 17/32
[52] U.S. Cl. ...................................................... 604/22
[58] Field of Search ................ 128/751, 752; 606/159, 606/170, 180, 171, 160, 161; 604/21, 22, 43

[56] References Cited

U.S. PATENT DOCUMENTS

| | | | |
|---|---|---|---|
| 3,945,375 | 3/1976 | Banko | 604/22 X |
| 4,073,287 | 2/1978 | Bradley et al. | 604/21 X |
| 4,316,465 | 2/1982 | Dotson | 604/22 |
| 4,320,761 | 3/1982 | Haddad | 604/22 X |
| 4,631,052 | 12/1986 | Kensey | 604/22 |
| 4,681,106 | 7/1987 | Kensey et al. | 606/180 |
| 4,696,667 | 9/1987 | Masch | 604/22 |
| 4,850,957 | 7/1989 | Summers | 604/22 |
| 4,857,045 | 8/1989 | Rydell | 604/22 |
| 4,857,046 | 8/1989 | Stevens et al. | 604/22 |
| 4,870,753 | 10/1989 | Don Michael et al. | 604/22 X |
| 4,950,238 | 8/1990 | Sullivan | 604/22 |
| 5,007,917 | 4/1991 | Evans | 604/22 X |
| 5,100,426 | 3/1992 | Nixon | 606/159 X |

Primary Examiner—V. Millin
Assistant Examiner—Sebastiano Passaniti
Attorney, Agent, or Firm—Grady J. Frenchick

[57] ABSTRACT

An apparatus for removing obstructions within a blood vessel of a patient using mechanical motion. The device has a catheter which is inserted into the vascular system at a convenient point, such as the femoral artery. The distal end of the catheter is advanced until it reaches the occlusion. A central lumen within the catheter contains a coil spring which functions as a flexible shaft to couple rotational motion provided by an electric motor or other source of rotational motion at the proximal end of the catheter to a cutting head at the distal end of the catheter. As the cutting head is rotated, the occlusion is milled away by the internal cutting edges of the cutting head. The particles cut from the occlusion are forced by the rotational motion of the cutting head into one of a number of outer lumens of the catheter. A vacuum is applied to the proximal end of some of the outer lumens to remove the particles from the patient's body.

15 Claims, 5 Drawing Sheets

ATHERECTOMY DEVICE

This is a continuation of copending application Ser. No. 07/521,413 filed on May 10, 1990, now abandoned.

BACKGROUND OF THE INVENTION

1. Field of the Invention

The present invention relates generally to medical devices used to remove occlusions within the vascular system, and more particularly, relates to medical devices used to remove occlusions within the vascular system using mechanical motion.

2. Description of the Prior Art

Devices for treating occlusions of the vascular system of a patient are commonly used in the art. The most popular type of such device is the balloon angioplasty catheter. It is a catheter which is inserted into the vascular system and advanced to the site of the occlusion. A balloon structure, located at the distal tip of the catheter, is inflated to enlarge the lumen at the site of the constriction.

Atherectomy devices are also catheters which are advanced within the vascular system to the site of an occlusion. However, the atherectomy device uses mechanical motion to remove the occlusion, thereby tending to prevent restenosis. U.S. Pat. No. 4,650,466 issued to Luther teaches an atherectomy device having a balloon with a rough outer surface. The balloon is inflated at the site of the occlusion, and rotated to abrade the occluding material.

U.S. Pat. No. 4,765,332 issued to Fischell, et al. discloses an atherectomy device which has a pair of knife blades. These blades are advanced beyond the occlusion and then drawn back to cut away the occluding material. An atherectomy device having a spinning head is shown in U.S. Pat. No. 4,664,112 issued to Kensey, et al.

In the use of each of these and other prior art devices, safety is a major concern. The cutting or abrading surface must not accidentally contact the wall of the vessel for fear of damaging the endothelialized tissue. Furthermore, great care must be exercised to prevent free particles of the occluding material from being conveyed by the blood stream and occluding a vessel in another portion of the vascular system.

SUMMARY OF THE INVENTION

The present invention is an atherectomy device which removes the occluding material using a rotating cutter head. The cutting edges of the rotating cutter head are beveled, such that milling of the occlusion only takes place within the cutter head. This ensures that the cutting surfaces will not accidentally contact the vessel wall.

The design of the rotating cutter head also tends to force the free particles of material into the catheter and away from the blood stream. A vacuum is applied to one or more of multiple outer lumens of the catheter to remove the free particles from the body of the patient. The use of multiple lumens improves reliability in case one of the lumens becomes occluded and tends to prevent collapse at bends in the catheter. Furthermore, the design of these multiple lumens tends to ensure that all of the free particles and a minimum of blood is vacuumed away from the body. One or more of the outer lumens may also be dedicated to irrigation or other functions.

A central lumen of the catheter is used for the passage of a coil spring which functions as a flexible shaft. This lumen is completely isolated from the outer lumens. Therefore, the central lumen tends to contain no blood or free particles of occluding material, permitting much tighter tolerances between the inside diameter of the central lumen and outside diameter of the coil spring. These tighter tolerances provide a much smoother and safer operation in the transfer of the rotational motion. However, it must be recognized that the diameter of the central lumen must be sufficiently larger than the outer diameter of the coil spring to prevent excess friction, heat buildup and binding.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENT

Figure 1:
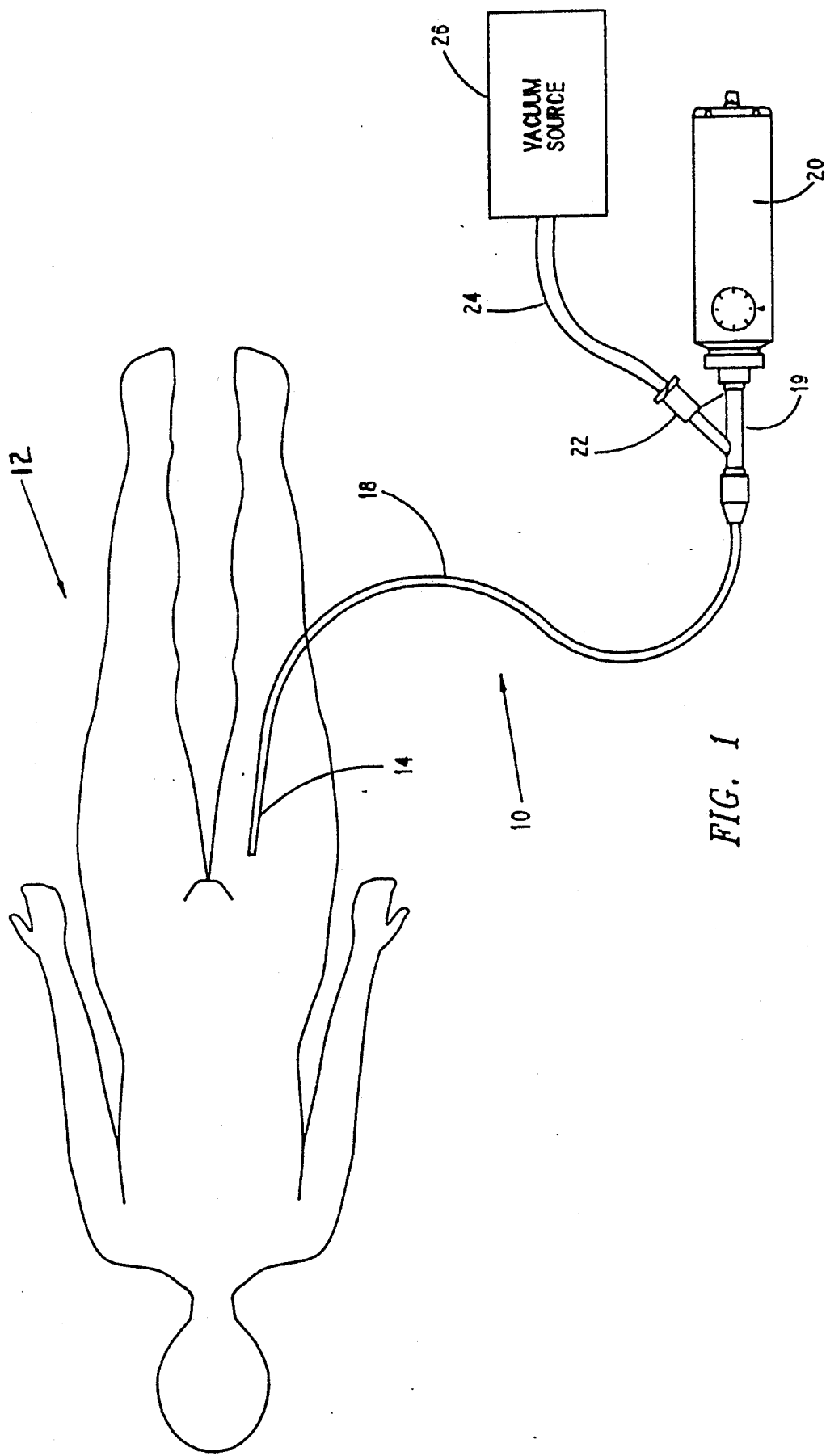
FIG. 1 is a schematic view of the use of the atherectomy device.

FIG. 1 is a schematic view showing operation of the atherectomy device 10 in a procedure involving patient 12. The distal tip of catheter 18 is inserted into a convenient incision 14 in the vascular system. In the preferred mode, this is at the femoral artery. Insertion is preferably over a previously positioned guidewire. The distal tip of catheter 18 is advanced under fluoroscopy until it comes into contact with the occlusion. While holding the distal tip of the catheter in contact with the occlusion, electric motor 20 is energized, thereby causing the cutter head of catheter 18 to rotate as explained in detail below.

Catheter 18 terminates at wye 19. The main branch of wye 19 accommodates electric motor 20 at its proximal end. Secondary branch 22 of wye 19 is coupled via tubing 24 to vacuum source 26. Upon activation of electric motor 20, vacuum source 26 must be activated to ensure that free particles of occluding material are removed from the vascular system of patient 12.

Figure 2:
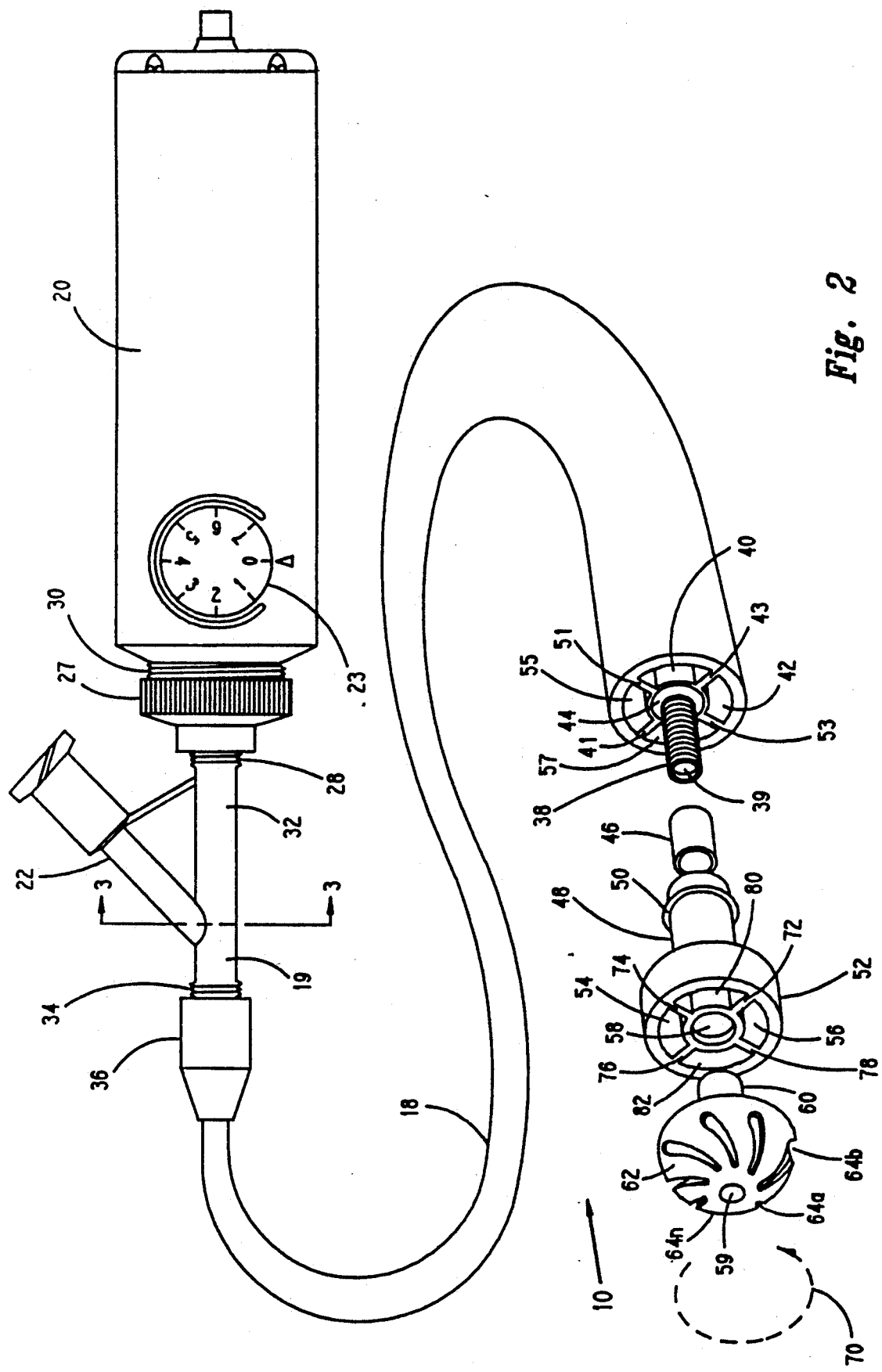
FIG. 2 is a partially exploded view of the atherectomy device.

FIG. 2 is a plan view of atherectomy device 10 having a partially exploded distal tip to show details of construction. Catheter 18 has an inner lumen 44 which accommodates coil spring 38. The rotational motion of electric motor 20 is transferred along catheter 18 by the rotation of coil spring 38. Because inner lumen 44 is essentially sealed at both proximal and distal ends, it will not contain any substantial contamination from blood or free particles of occluding material. Therefore, the inside diameter of inner lumen 44 may be made to be very nearly that of the outside diameter of coil spring 38. This greatly promotes smooth operation of the torque transfer and tends to prevent lateral motion. The speed of electric motor 20 is readily adjustable via speed control 23. Lumen 39 of coil spring 38 provides for insertion over a guidewire not shown for clarity.

Electric motor 20 is coupled to adapter 27 using male threads 30. Coil spring 38 is coupled to the rotor of electric motor 20 (not shown). Adapter 27 is coupled to main branch 32 of wye 19 using male threads 28. Secondary branch 22 is coupled to vacuum source 26 (see also FIG. 1). Wye 19, which is preferably of a rigid material, is coupled to catheter 18 using coupling 36 and threads 34 as shown.

Figure 3:
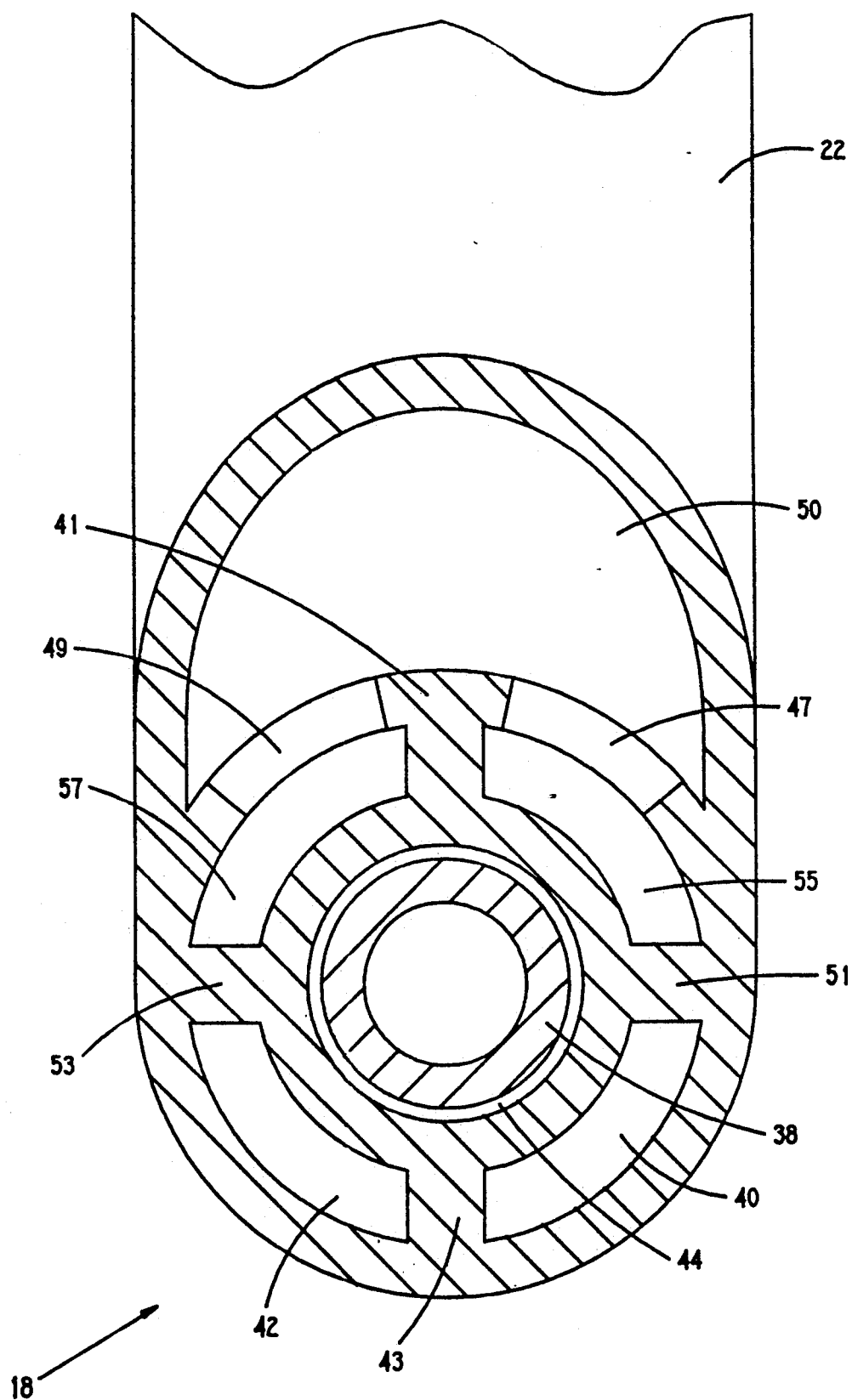
FIG. 3 is a sectioned view of the atherectomy device showing details of the construction of the coupling between the two semicircular outer lumens and the vacuum source.

Catheter 18 is preferably extruded of a flexible material such as polyurethane with the cross section as shown (see also FIG. 3). It contains inner lumen 44, as discussed above, and a number of partially circular outer lumens 40, 42, 55 and 57. A minimum of four such outer lumens is recommended, but the present invention is not intended to be limited to four outer lumens. As explained in greater detail below, one or more of outer lumens 40, 42, 55 and 57 are used to evacuate free particles of occluding material using vacuum source 26.

Proximal end 48 of stationary portion 52 of the distal tip is press fit into the distal end of catheter 18. Flange 50 serves to hold it in place. Central lumen 58 of stationary portion 52 aligns with inner lumen 44 of catheter 18. Similarly, outer lumens 54, 56, 80 and 82 of stationary portion 52 align with outer lumens 40, 42, 55 and 57 of catheter 18, respectively. Bushing 46 serves as the bearing surface between coil spring 38, when rotated, and stationary portion 52.

Cutter head 62 is mounted distal of stationary portion 52. Coil spring 38 frictionally engages the inner surface of hollow shaft 60 of cutter head 62. In that manner rotational motion of coil spring 38 results in the rotation of cutter head 62. The cutting operation is performed by inwardly beveled cutting edges 64a-64n. As explained above, the cutting edges are inwardly beveled to protect the vessel wall. When cutter head 62 is rotated in the direction of arrow 70 and in contact with occluding material, the material is milled away with the free particles being forced in a proximal direction by cutting edges 64a-64n. Aperture 59 of cutter head 62 corresponds with lumen 39 of coil spring 38 for passage of a guidewire.

FIG. 3 is a view of wye 19 in partial cross section to show the detail of particle removal. Inner lumen 44 contains coil spring 38 as explained above. The extrusion of catheter 18 produces outer lumens 40, 42, 55 and 57 as also explained above. Notice that septal areas 41, 43, 51 and 53 divide and separate the outer lumens 40, 42, 55 and 57, as well as providing structural support to the outer surface of catheter 18.

Slots 47 and 49 in the outer surface of catheter 18 provide a fluid path between semicircular outer lumens 55 and 57 and the inner lumen of secondary branch 22. As explained above, vacuum source 26 is coupled to secondary branch 22 (see also FIG. 1). The use of the multiple lumen design greatly increases reliability and minimizes the blood that is attracted to vacuum source 26.

Outer lumens 40 and 42 are shown as isolated from outer lumens 55 and 57. This permits outer lumens 40 and 42 to perform functions different from outer lumens 55 and 57 as explained below. However, outer lumens 40 and 42 may also be used for aspiration by skinning back the outer covering of catheter 18 or septal areas 43, 51 and 53 in the region of secondary branch 22.

Figure 4:
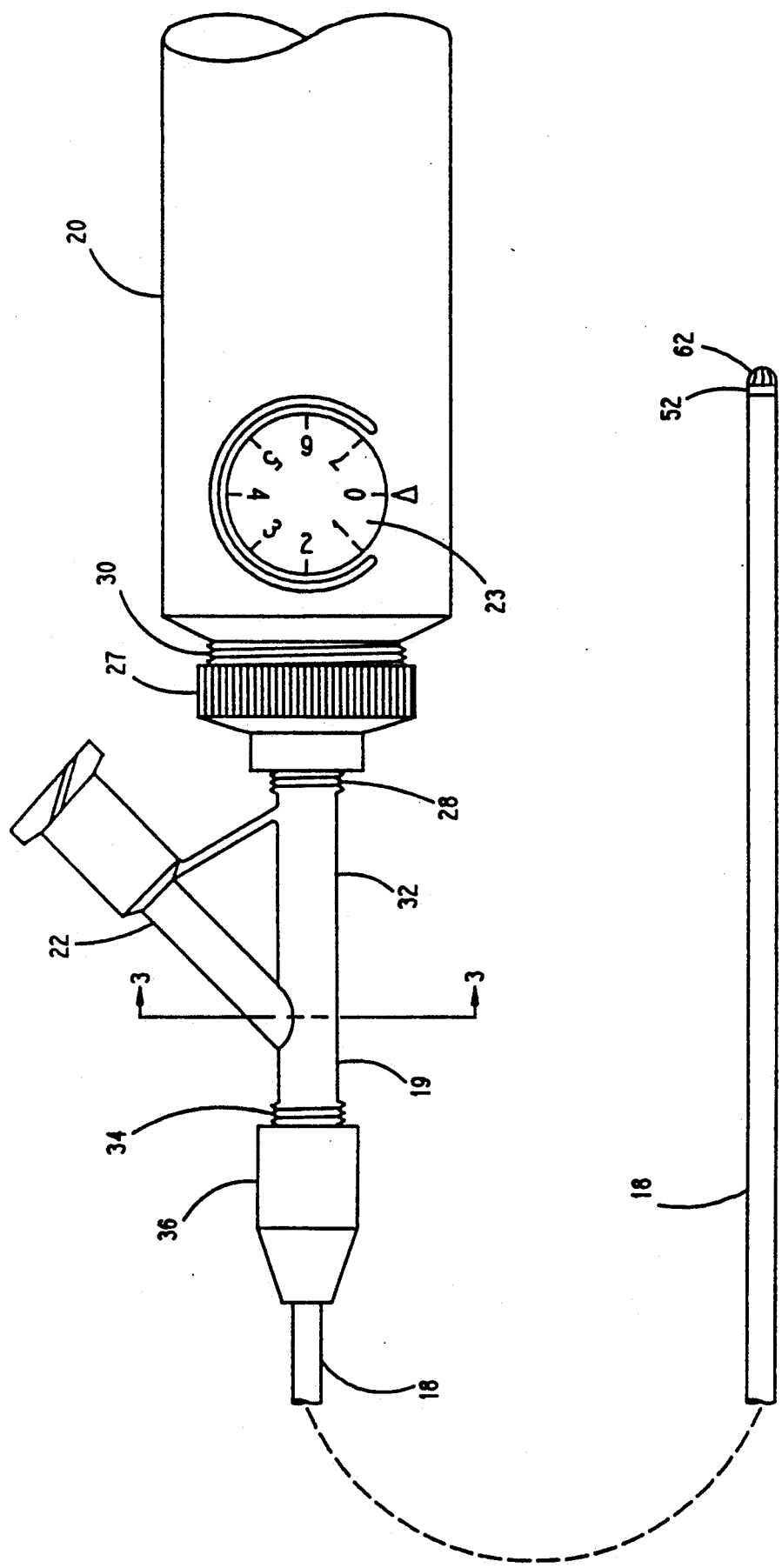
FIG. 4 is a plan view of the atherectomy device.

FIG. 4 is a plan view of atherectomy device 10 wherein all numerals correspond to those elements previously described.

Figure 5:
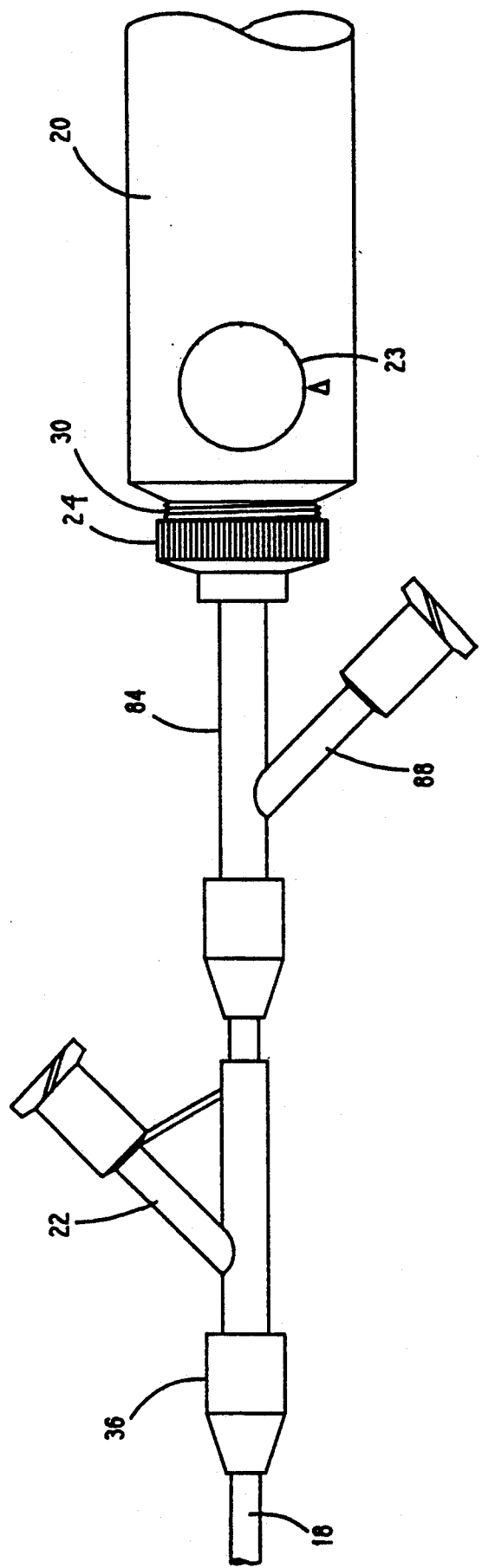
FIG. 5 is a plan view of the proximal end of the atherectomy device using a second wye for irrigation purposes.

FIG. 5 is a plan view of the proximal end of the atherectomy device wherein second wye 84 is added between wye 19 and motor 20 as shown. Second wye 84 has secondary branch 88 which may be used to couple to one or more of the outer lumens (i.e., 40, 42, 55 and 57) as explained above. Secondary branch 88 may be coupled to an irrigation source for example. All other elements are as previously described.

Having thus described the preferred embodiment, those of skill in the art will be readily able to apply the teachings found herein to other embodiments without deviating from the scope of the claims hereto attached.

We claim:

1. An atherectomy device for removing occluding material in a vascular system, comprising:
   a. a catheter having a proximal end and distal end;
   b. transferring means for transferring rotational motion from said proximal end of said catheter to said distal end of said catheter;
   c. means attached to said proximal end of said catheter and said transferring means for rotating said transferring means with respect to said catheter;
   d. occluding material cutting means attached to said distal end of said catheter and said transferring means which rotates with respect to said distal end of said catheter in response to rotation of said transferring means for excising said occluding material, said occluding material cutting means comprising a cutter head having cutting edges extending inwardly in a radial direction and being beveled such that said excising of said occluding material takes place within said cutter head; and
   e. removing means attached to said catheter for removing free occluding material.

2. An atherectomy device according to claim 1 wherein said cutting head further comprises a central bore adapted to receive a guidewire.

3. An atherectomy device according to claim 1 wherein said removing means further comprises a vacuum source attached to said proximal end of said catheter.

4. An atherectomy device according to claim 3 wherein said removing means further comprises a plurality of lumens from said proximal end to said distal end of said catheter attached to said vacuum source.

5. An atherectomy device according to claim 4 wherein said removing means further comprises a plurality of beveled cutter edges attached to said cutter head.

6. An atherectomy device according to claim 1 which comprises a plurality of lumens from said proximal end to said distal end of said catheter for performing a function other than removing occluding material.

7. An atherectomy device according to claim 6 wherein said different function is irrigation.

8. An atherectomy device for removing occluding particles in a vascular system, comprising:
   a. a catheter having a proximal end, a distal end, a plurality of catheter outer lumens and a catheter central lumen isolated from said plurality of outer lumens;
   b. transferring means in said catheter central lumen for transferring rotational motion from said proximal end of said catheter to said distal end of said catheter;

c. means attached to said proximal end of said catheter and said transferring means for rotating said transferring means with respect to said catheter;

d. occluding particles cutting means attached to said distal end of said catheter and to said transferring means which rotates with respect to said distal end of said catheter in response to rotation of said transferring means for excising said occluding material, said occluding particle cutting means comprising a cutter head having cutting edges extending inwardly in a radial direction and being beveled such that said excising of said occluding material takes place within said cutter head; and e. removing means attached to said catheter for removing free occluded particles.

9. The atherectomy device of claim 8 wherein said removing means comprises a vacuum source in communication with at least one of said plurality of catheter outer lumens.

10. The atherectomy device of claim 8 further comprising irrigation means in communication with at least one of said plurality of catheter outer lumens for supplying irrigation fluid to said vascular system.

11. The atherectomy device of claim 8 wherein said cutter head further comprises a central bore adapted to receive a guidewire.

12. An atherectomy device according to claim 8 wherein said occluding particle cutting means further comprises a stationary member having a stationary member central lumen and a plurality of stationary member outer lumens attached to said catheter distal end so that said stationary member central lumen aligns with said catheter central lumen and said plurality of stationary member outer lumens align with said plurality of catheter outer lumens, and wherein said stationary member central lumen receives said cutter head.

13. An atherectomy device according to claim 12 wherein said cutter head further comprises a hollow shaft having an inner surface, and wherein said transferring means frictionally engages the inner surface of said hollow shaft.

14. A method of excising occluding material in a vascular system, comprising:

a. inserting a catheter into said vascular system, said catheter comprising rotatable cutting means comprising a cutting head having a plurality of cutting edges extending inwardly in a radial direction and being beveled;

b. guiding said catheter to the vicinity of said occluding material;

c. imparting rotation to said cutting means to cut said occluding material within said cutting head; and d. removing said cut occluding material from said vascular system.

15. The method of claim 14 wherein said catheter is guided to the vicinity of said occluding particles with the aid of a guidewire in said catheter.

* * * * *